(12) United States Patent
Snow et al.

(10) Patent No.: US 9,892,655 B2
(45) Date of Patent: Feb. 13, 2018

(54) METHOD TO PROVIDE FEEDBACK TO A PHYSICAL THERAPY PATIENT OR ATHLETE

(71) Applicants: Judy Sibille Snow, Los Altos, CA (US); Robert James Snow, Los Altos, CA (US)

(72) Inventors: Judy Sibille Snow, Los Altos, CA (US); Robert James Snow, Los Altos, CA (US)

( * ) Notice: Subject to any disclaimer, the term of this patent is extended or adjusted under 35 U.S.C. 154(b) by 678 days.

(21) Appl. No.: 13/777,465

(22) Filed: Feb. 26, 2013

(65) Prior Publication Data

US 2014/0147820 A1    May 29, 2014

Related U.S. Application Data

(60) Provisional application No. 61/730,773, filed on Nov. 28, 2012.

(51) Int. Cl.
*G09B 19/00*    (2006.01)
*G06F 19/00*    (2018.01)
*G06K 9/00*    (2006.01)

(52) U.S. Cl.
CPC ..... *G09B 19/0038* (2013.01); *G06F 19/3418* (2013.01); *G06F 19/3481* (2013.01); *G06K 9/00342* (2013.01)

(58) Field of Classification Search
CPC ............ A63B 24/0075; G09B 19/0038; G06F 19/3418; G06F 19/3481; G06K 9/00342
USPC ......................................................... 434/247
See application file for complete search history.

(56) References Cited

U.S. PATENT DOCUMENTS

| | | | | |
|---|---|---|---|---|
| 6,007,459 A | * | 12/1999 | Burgess | 482/4 |
| 7,348,963 B2 | | 3/2008 | Bell | 345/156 |
| 7,658,695 B1 | * | 2/2010 | Amsbury et al. | 482/8 |
| 7,927,216 B2 | | 4/2011 | Ikeda et al. | 463/38 |
| 7,993,291 B2 | * | 8/2011 | Karkanias et al. | 602/5 |

(Continued)

FOREIGN PATENT DOCUMENTS

WO    WO 2010/062521    6/2010

OTHER PUBLICATIONS

Gregorij Korillo; Real-time 3D Avatars for Tele-rehabilitation in Virtual Reality; Medicine Meets Virtual Reality, v18, pp. 290-296.*

(Continued)

*Primary Examiner* — Eddy Saint-Vil
(74) *Attorney, Agent, or Firm* — John H. Runnels (57) ABSTRACT

A process is disclosed to visually capture a person doing a set of steps for an exercise, and then to compare that person during exercise to those steps, measuring the results. Each exercise is tailored to the individual patient, rather than to an "ideal" or "generic" standard. This flexibility allows a physical therapist to optimize treatment for patients progressively, and/or to accommodate multiple physical problems in one patient. This invention can be used as a medical software product under the guidance of a physical therapist for rehabilitation exercises. It may alternatively be used as a fitness or sports training device under the guidance of a trainer or coach. By providing visual data and tracking results, it enhances communication between the physical therapist and the patient (or trainer and athlete), and optionally, the physician.

20 Claims, 10 Drawing Sheets

(56) References Cited

U.S. PATENT DOCUMENTS

| | | | |
|---|---|---|---|
| 8,152,640 B2 | 4/2012 | Shirakawa et al. | 463/36 |
| 8,166,421 B2 | 4/2012 | Magal | 715/863 |
| 8,213,680 B2 | 7/2012 | Fitzgibbon et al. | 382/103 |
| 8,223,088 B1 | 7/2012 | Gomez et al. | 345/7 |
| 8,228,315 B1 | 7/2012 | Starner et al. | 345/175 |
| 2009/0023555 A1* | 1/2009 | Raymond | G06Q 10/10 482/9 |
| 2010/0134408 A1* | 6/2010 | Palsbo | G06F 3/016 345/156 |
| 2011/0054870 A1* | 3/2011 | Dariush | G06F 3/011 703/11 |
| 2012/0143358 A1 | 6/2012 | Adams et al. | 700/92 |
| 2012/0162065 A1 | 6/2012 | Tossell | 382/103 |
| 2012/0259648 A1* | 10/2012 | Mallon | G06F 19/3418 705/2 |
| 2012/0293548 A1 | 11/2012 | Perez et al. | 345/633 |
| 2013/0006659 A1* | 1/2013 | Mills | 705/2 |
| 2013/0123667 A1* | 5/2013 | Komatireddy | A61B 5/0002 600/595 |
| 2013/0252216 A1* | 9/2013 | Clavin | G09B 19/0038 434/257 |

OTHER PUBLICATIONS

Chien-Yen Chang et al., "Towards Pervasive Physical Rehabilitation Using Microsoft Kinect," International Conference on Pervasive Computing Technologies for Healthcare (Pervasive Health), San Diego, California, USA (May 2012).

Joint Orientation, http://msdn.microsoft.com/en-us/library/hh973073.aspx, accessed Nov. 8, 2013.

* cited by examiner

METHOD TO PROVIDE FEEDBACK TO A PHYSICAL THERAPY PATIENT OR ATHLETE

CROSS-REFERENCE TO RELATED APPLICATIONS

This application claims priority under 35 U.S.C. § 119(e) from U.S. Provisional Application Ser. No. 61/730,773, filed Nov. 28, 2012, entitled "Method to Provide Feedback to a Physical Therapy Patient or Athlete," the contents of which are fully incorporated by reference herein.

TECHNICAL FIELD

This disclosure relates generally to electronic capture, storage and comparison analysis of body position for purposes of ascertaining the correct position of each step during exercise repetitions.

BACKGROUND OF THE INVENTION

Physical Therapy Background

Physical therapists currently provide significant assistance to patients recovering from accidents and injuries. Typically, physical therapists will work with the patient twice a week, conducting a 45-minute physical therapy session with the patient. During this session, the physical therapist assesses the individual patient's range of motion and strength. The physical therapist will then outline a preferred set of exercises in order for the patient to gain further control of various muscle groups. Normally, the physical therapist will provide an exercise regimen for the patient to undergo while the physical therapist is not present. It is quite common for the physical therapist to demonstrate the exercises to the patient and coach her in their execution to ensure that the patient understands them properly, and then request that the patient carry out the exercise a number of times each day. For example, the patient might be instructed to move an arm through a certain range of movement for ten repetitions at three separate times during the day. During the next visit, the physical therapist will assess whether she has improved her range of motion and prescribe advancing sets of exercise regimens in order to restore full mobility.

Physical Therapy Instruction

When a physical therapist (or assistant) is with a patient, the patient is observed for quality and quantity of therapeutic exercise. The patient is frequently assigned exercises to perform on her own. The instructions consist primarily of paper sketches showing each exercise step, sometimes with patient-specific modifications noted in the sketch. Enhancements to these instructions can include two dimensional photos or videos of a model performing the assigned exercise. Patient-specific instructions are still noted separately because the model represents an "ideal" or "generic" standard, rather than an exercise specifically tailored for the individual patient. Unfortunately, the physical therapist does not currently have a way to easily monitor the exercises that the patient performs on their own.

Exercise or Fitness Instruction

When a person learns an exercise, he seeks to imitate an athlete or a model performing the exercise via a picture, a video, or live in a group or private exercise class. A live instructor may be able to provide real-time feedback to the student, possibly making unique modifications for that person. Automated exercise feedback attempts to duplicate real-time feedback with various apparatuses, but the goal is still an "ideal" or "generic" standard.

Video Games

Since Microsoft Corporation released the Kinect™ motion sensing input device in November 2010, numerous software games have used the Kinect™ to analyze a user's movements in three dimensions, and compare them to a pre-defined goal. One example is the Dance Central™ music video game by Harmonix Music Systems. See Pat Pub No US 2012/0143358. Another example is the Your Shape: Fitness Evolved system by Ubisoft Entertainment. Other examples are themed by sport, reflecting ball movement in tennis, for example, based on the movement of the arm during the swing. Goals are pre-determined. Comparisons, normalized for varying body sizes, are made to an "ideal" standard.

Other examples of video game technology that preceded the Kinect are the Nintendo Wii™ Remote (See U.S. Pat. No. 7,927,210, the Nintendo Wii Fit™ Balance Board (See U.S. Pat. No. 8,152,640), and the Sony PlayStation Move™ (See EP 2356545). As shown in the referenced patents, rehabilitation video games have been created based on this technology. Video games based on the Nintendo or Sony gaming systems require the user to either hold a sensor or stand on a Balance Board sensor.

Sensor-Based Systems

Figure 1A:
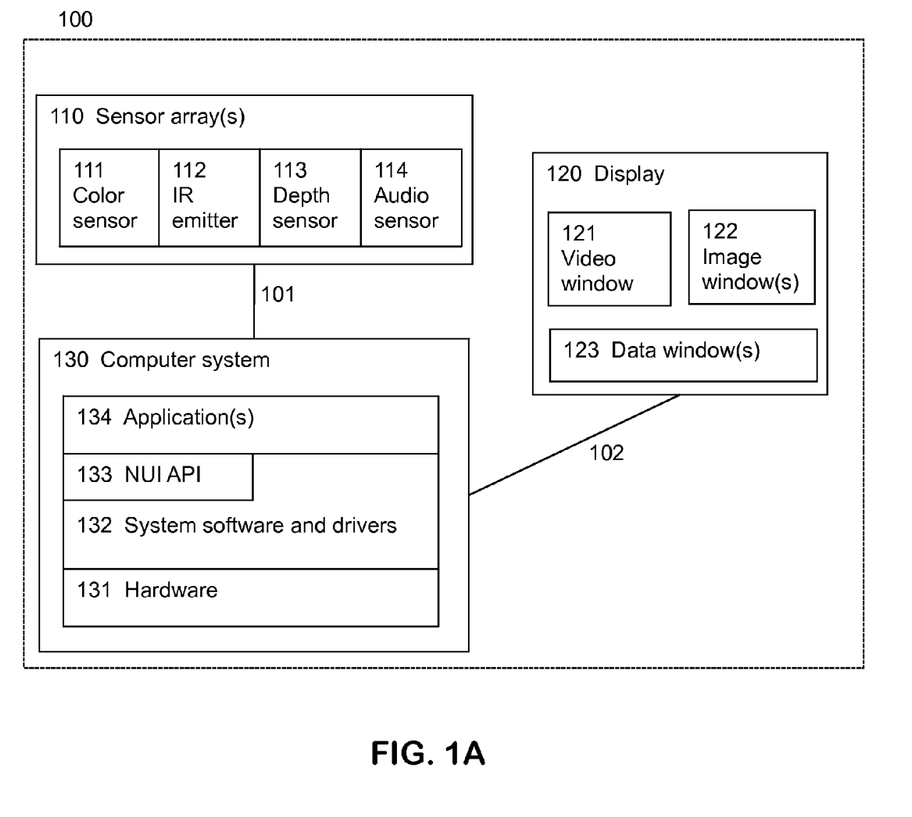
FIG. 1A illustrates schematically one embodiment of a sensor-based system.

A sensor-based system is illustrated schematically in FIG. 1A. This system has at least one sensor array 110 with a color sensor camera 111, an infrared (IR) emitter 112, a depth sensor 113, an audio sensor 114, and a processor (not shown). In one embodiment, the RGB camera 111 delivers a three-color (Red, Green, Blue) image stream. The infrared emitter 112 combines with the infrared depth sensor 113 to deliver a depth stream. These data streams provide a computer system 130 the ability to recognize objects in the camera's field of view in three dimensions. The multi-microphone audio sensor 114 parses voices and sound input, while simultaneously extracting and nullifying ambient noise, delivering an audio stream. A processor with commercially-available, proprietary software can coordinate these input streams.

FIG. 1A also shows a display 120 and a computer system 130, which may or may not be combined in a single unit such as an all-in-one PC, a laptop, or a tablet. A television connected to the computer system could also serve as the display 120. Physical connectivity is provided by an internal or external system bus such as a USB cable 101 or an HDMI cable 102. Software running on the computer system 130 comprises system software and drivers 132, a Natural User Interface (NUI) Application Programming Interface (API) 133, and one or more application(s) 134. A sophisticated, commercially-available NUI software library and related tools help developers use the rich form of natural input coming from a sensor array to react to real-world events.

Kinect Environment

Microsoft's Kinect™ is a peripheral device that connects as an external interface to Microsoft's Xbox 360™ or to Microsoft Windows™ computers. The Kinect™ and the associated programmed computer or Xbox sense, recognize, and utilize the user's anthropomorphic form so the user can interact with software and media content without the need for a separate controller. A three-dimensional user interface enabled by Kinect™ hardware is disclosed in U.S. Pat. No. 8,106,421, and a general interactive video display system is disclosed in U.S. Pat. No. 7,348,963.

Microsoft provides a proprietary software layer (e.g., U.S. Pat. No. 8,213,080 to realize the Kinect's capabilities.

Developers can alternatively use Microsoft's Kinect Software Development Kit (SDK), or various open source software libraries. The former will generally be used in the present description.

When the Microsoft Kinect SDK is used with a Kinect for Windows sensor array 110, the computer system 130 should comply with Microsoft's system requirements for hardware 131 and system software 132. Details of the Microsoft Kinect SDK environment are referenced on the Microsoft website, http://msdn.microsoft.com/en-us/library/jj131023.aspx (webpage visited on Nov. 16, 2012), and can be summarized as follows: Hardware 131: 32 bit (x86) or 64 bit (x64) dual-core 2.66-GHz or faster processor; 2 GB RAM; dedicated USB 2.0 bus; graphics card that supports DirectX 9.0c; Microsoft Kinect for Windows sensor; system software and drivers 132: Microsoft Windows 7 or 8, including the APIs for audio, speech, and media; DirectX end-user runtimes (June 2010); Kinect microphone array and DirectX Media Object (DMO); audio and video streaming controls (color, depth, and skeleton); device enumeration functions that enable more than one Kinect; Kinect NUI API 133: Skeleton tracking, audio, color and depth imaging.

Application(s) 134 may require or benefit from additional hardware 131, such as local data storage, audio output devices, or Internet connectivity. Additional system software and drivers 132 may be required to support this hardware. An application 134 may also employ other features supported by system software, such as the Windows Graphical User Interface (GUI) libraries.

Skeletal Tracking

A sensor-based system can provide a framework for determining positional information of a user's body, capturing motion for purposes of analysis. Various systems exist for capturing motion through sensors. For example, a system combining a camera with a depth sensor can be used to determine positional information about the user's body in three dimensions and produce a skeleton model. In other systems, transducers attached to the user's body are used to detect the positions of the user's limbs and produce a skeleton model. Other systems use infrared pointing devices, other motion tracking peripherals, or multiple cameras to enhance positional information in three dimensions.

As used herein, the terms "joint", "bone", and "skeleton" are intended to have the meaning that one of skill in the art of motion capture and animation would ascribe to them. For example, a skeleton can comprise bones, but the number of bones and their positions are a function of the motion capture equipment and software libraries, and may differ from the number and positions of bones that an anatomist or physician would recognize in a human skeleton. Similarly, a joint can be the distal endpoint of a single bone (e.g., a fingertip or the head), and need not necessarily be at a point where two bones come together.

Figure 1B:
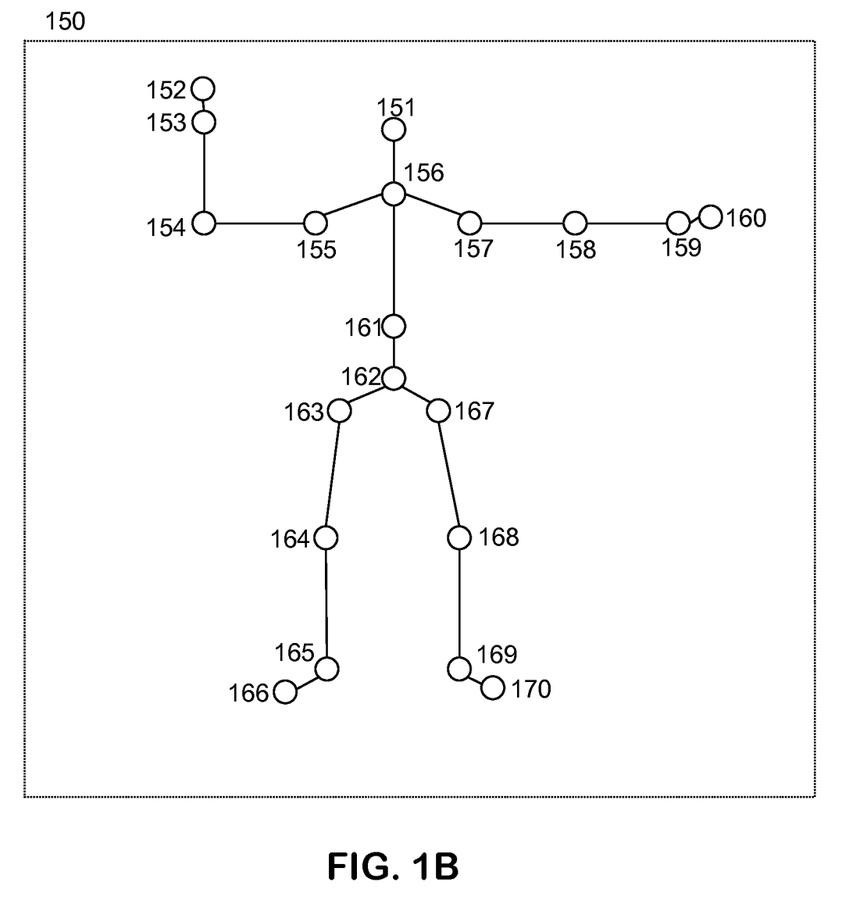
FIG. 1B illustrates schematically a skeletal data model provided by a camera system and NUI API in accordance with certain embodiments.

As schematically illustrated in FIG. 1B, a typical skeletal model 150 is a collection of joints 151 through 170, and lines representing the bones connecting the joints. The model's output is a data structure that includes coordinates describing the location of each joint and connected lines of a human body's bones. An example for skeletal model representation and generation thereof can be found in US Patent Application Publication US 2010/0197399 to Geiss.

The Microsoft Kinect NUI API 133 includes skeletal tracking as described in US 2012/0162065 to Tossell, et al. In addition, it provides bone orientation in two forms. One is an absolute orientation in Kinect camera coordinates using the depth stream to provide raw data. The second is a hierarchical rotation, based on a bone relationship as defined in the skeleton joint structure. In the reference http://msdn.microsoft.com/en-us/library/hh973073.aspx (webpage visited on Nov. 16, 2012), Microsoft provides a detailed explanation of joint orientation and hierarchical rotation for developers of avatar animation, the stated target audience.

Comparison to High-End Sensor Technology

The Kinect sensor is sufficiently accurate to use in physical rehabilitation. The University of Southern California recently published a comparison of physical rehabilitation using the Kinect versus the substantially more expensive NaturalPoint OptiTrack™ optical system. Commercially-available physical rehabilitation software is not currently available for either system; the USC researchers wrote custom software to specifically compare External Rotation tracking on both systems. "External Rotation" is a common therapeutic exercise for injured shoulders, well known to physical therapists. The authors noted that the expensive, highly accurate OptiTrack system requires many reflective sensors to be attached to the patient's body, limiting the mobility and comfort of patients. The experiment results "showed that the Kinect can achieve competitive motion tracking performance as OptiTrack and provide 'pervasive' accessibility" for patients. See Chien-Yen Chang et al., "Towards Pervasive Physical Rehabilitation Using Microsoft Kinect," *International Conference on Pervasive Computing Technologies for Healthcare* (Pervasive Health), San Diego, Calif., USA, May 2012.

There is an unfilled need in physical therapy for an improved device which can both monitor an exercise that is specifically designed for an individual patient, and provide enhanced real-time feedback to the patient. Better feedback could result in better patient compliance and better outcomes, measured in healing time and reduced re-injuries, which could reduce healthcare costs and enable physical therapists to treat more patients.

DISCLOSURE OF THE INVENTION

We have discovered a process to create and then implement a set of exercises that is tailored uniquely for each patient. The novel process visually captures a person doing a set of steps for an individually-tailored exercise, and then compares that same individual's motions during exercise to those steps, measuring and comparing the results. The data that is captured includes a picture, an optional video, data about the position of the body in three dimensions, and data about the goals and tolerances of the exercise. The system compares an individual's motions during exercise to a previously-captured version of the same individual performing the exercise properly, rather than comparing the individual's motions to idealized or generic exercises as performed by a model or athlete. The system can provide immediate feedback to the user when an exercise is not being performed properly, specific feedback explaining what the user should do differently in order to perform the exercise correctly. The invention tailors each exercise to the individual patient, not to an "ideal" or "generic" standard. Instead of trying to imitate someone else, the patient sees himself or herself in the exact position the therapist requires for each step. This flexibility allows the therapist to optimize treatment for patients progressively. The flexibility of the novel system readily accommodates the treatment of multiple physical problems in the same patient, a therapeutically important goal that has been difficult or impossible to achieve using models performing "ideal" or "generic" versions of an exercise.

The novel process, realized in one or more software applications, can be used as a medical software product under the guidance of a physical therapist for rehabilitation exercises. By providing visual data and tracking results, it enhances communication between the physical therapist and the patient, and optionally, the physician.

The disclosed process creates a set of exercises that is unique to each patient by capturing and storing a 3D representation of each step of each exercise, recording a video of the patient performing each exercise, and setting goals and tolerances for each exercise. It contains software to review the exercises created for each patient. It contains software to provide a virtual mirror—as the patient watches herself exercise, she sees when each step is done properly, in real-time. The software can analyze exercise results and present them to the physical therapist for the individual patient, or aggregate them for the medical community.

In a preferred embodiment, cloud storage and secure Internet applications facilitate exercise data transfer between the physical therapist's clinic and the patient's home or any other location.

This invention enables the patient to complete the prescribed exercises accurately and completely. It enables the physical therapist to better motivate the patient and optimize treatment. It offers an advantage over current exercise sketches, photos or videos by providing immediate and automated, tailor-made feedback to help the individual patient.

An alternative embodiment provides personalized general movement training for sports or fitness, guided by a trainer or coach in lieu of a physical therapist. In such a case, all references to "patient" can be replaced with "person" or "athlete," and all references to "physical therapist" or "therapist" can be replaced with "trainer," "personal trainer," or "coach." "Athlete" should be understood in a broad sense, to include people engaged not only in traditional athletic events, but also in various professional, amateur, recreational, fitness, training, and other physical activities.

DETAILED DESCRIPTION OF THE INVENTION

The applications we have developed implement a core workflow process for the physical therapist and the patient. Additional discussion below concerns the auxiliary functions of data collection, aggregation, analysis, and accuracy.

Core Workflow

The physical therapist creates a set of exercises unique to each patient by capturing and storing a 3D representation of the patient performing each step of each exercise correctly, recording a video of the patient performing each exercise correctly, and setting goals for each exercise. The patient reviews the prescribed steps, video, and goals. The patient exercises while tracked by a camera-based sensor system, receiving automated feedback in real-time. The physical therapist views the results.

EMBODIMENTS FOR CARRYING OUT THE INVENTION

An application 134 that embodies the core workflow uses a sensor-based system 100, as illustrated schematically in FIG. 1A. The system comprises one or more sensor array(s) 110, a display 120, and a computer system 130. A preferred embodiment utilizes a 3D camera sensor, such as the Microsoft Kinect camera, as sensor array 110 to track patient movement. This embodiment utilizes a NUI API 133 from the Microsoft Kinect Software Developer Kit (SDK) on computer system 130 to determine skeletal joint position. A comfortably large display 120 contains a video window 121 in which the patient can view herself or a video of herself; the other image window(s) 122 show each prescribed exercise step. Other embodiments with smaller displays with different window configurations may be desirable in some circumstances.

Another embodiment of the present invention employs smaller displays or head-mounted displays, such as those of the Google Project Glass or Microsoft's event augmentation. See, e.g., U.S. Pat. No. 8,223,088, U.S. Pat. No. 8,228,315, and U.S. patent application publication no. 2012/0293548. In such an embodiment, the patient can wear glasses to see a virtual display instead of looking at a fixed display some distance away. The patient then has freedom to turn around or turn to the side while exercising, and still see the video—rather than, for example, move a Kinect to the side or behind while still trying to look at a screen. The patient can even look down and see himself or herself exercise from the side. One such embodiment resembles a pair of normal eyeglasses, in which the lens is replaced by a heads-up display. Other embodiments will allow integration of the display into people's normal eyewear.

In one embodiment, the physical therapist creates exercises with the patient in her office and then has the patient exercise using the same computer system, alleviating the need to move images, video, and data to another computer system. Both the therapist and the patient can review the exercises and results on this computer system.

Figure 2A:
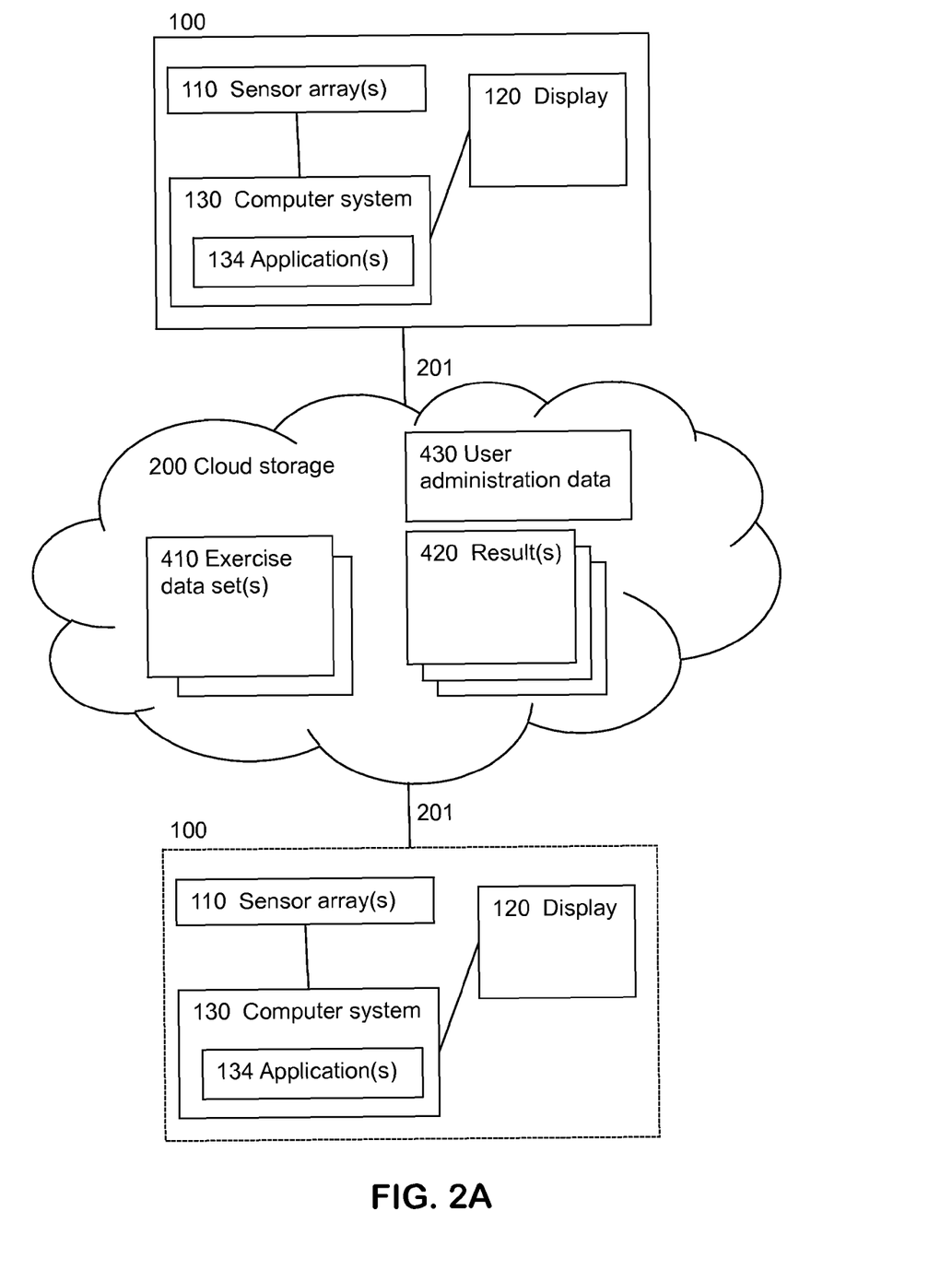
FIG. 2A illustrates schematically data movement and cloud storage between two or more sensor-based systems.

A second embodiment, shown in FIG. 2A, allows the patient to exercise at a remote location, such as their home. The physical therapist can create the exercises with the patient on a sensor-based system 100 in her office. The patient can exercise on another sensor-based system 100 in different location. In this embodiment, the exercise data sets(s) 410 are transferred from the creation system and then retrieved on the exercise system, e.g. via cloud storage 200. Likewise, the result(s) 420 are transferred from the exercise system, e.g. via cloud storage 200, and then retrieved from elsewhere. Secure user administration 430 and data transmission 201 systems known in the art are used for this purpose. This embodiment enables real-time compliance tracking of a remote patient by the physical therapist.

Figure 2B:
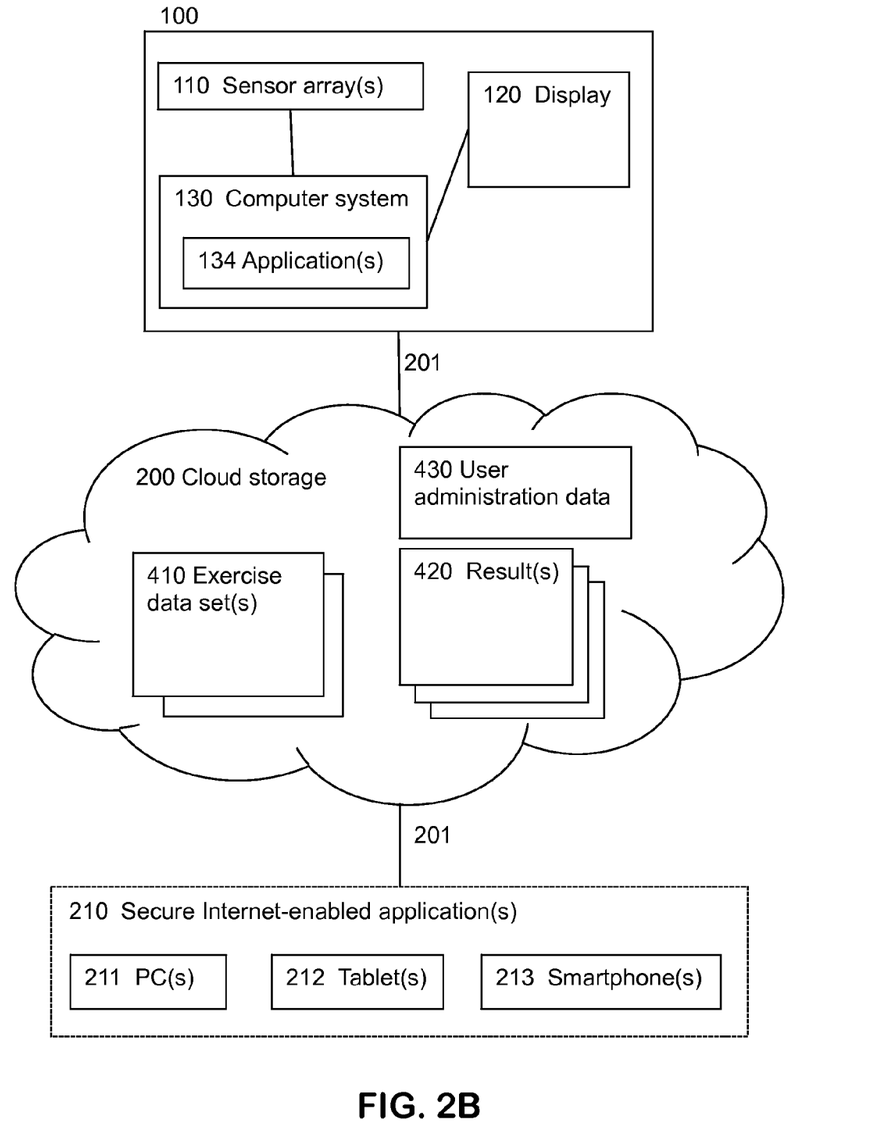
FIG. 2B illustrates schematically cloud storage and data access with secure internet-enabled browser applications on various devices.

An unexpected surprise of using cloud storage is realized in a third embodiment, illustrated in FIG. 2B, The sensor-based system 100 needed to create and exercise is not required to review exercises and results. In fact, any device capable of viewing images on the Internet can be used with a secure Internet-enabled application 210, such as a browser application, using standard connectivity 201. Examples of Internet-enabled devices include PC(s) 211, tablet(s) 212 and smartphone(s) 213. Standard HIPAA-compliant user authentication and authorization procedures are used with algorithms known in the art to view the media across standard transmission 201. This embodiment enables more flexibility to review goals, images, and video, and to view results.

A physical therapist can also use a commercially available secure Internet-enabled application 210, such as Skype, to communicate with a remote patient. Using video conferencing simultaneously with the disclosed software provides a tool, previously unavailable to physical therapists, that allows them to remotely help patients. The invention can be used as a tool in telemedicine by physical therapists as state laws and insurance reimbursements become supportive.

Create

A physical therapist works with the patient to create an individually-tailored exercise by capturing steps, capturing video, and setting goals (such as the number of repetitions) for the patient. Instead of a paper handout with sketches for each step in the exercise, the therapist properly positions the patient for each step. When positioning the patient, the therapist can take into account multiple injuries or other unique physical limitations of the individual patient. As the patient progresses in therapy, exercises can be modified, steps and video can be recaptured, goals can be increased, and additional exercises can be added. Each exercise is unique to the specific patient, and is not based on the performance of an "ideal" or "generic" model or athlete.

Figure 3A:
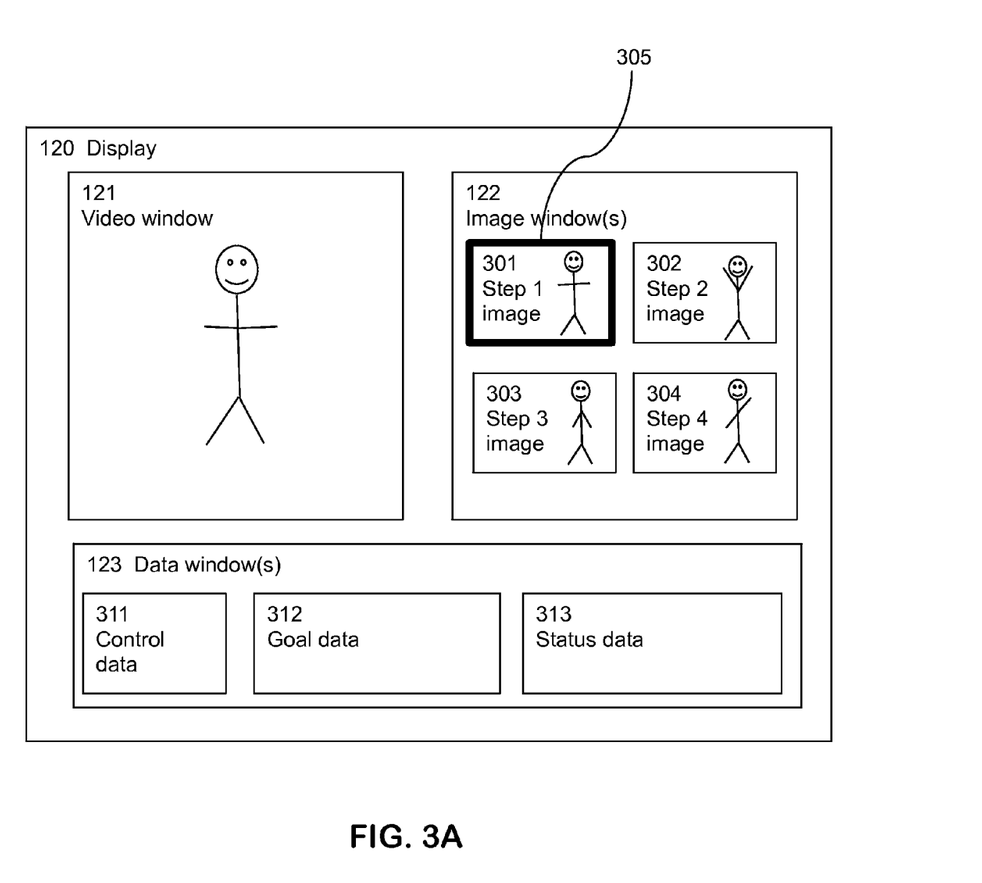
FIG. 3A illustrates schematically an example of a user interface to create, review, or exercise.

One embodiment of a user interface on a sensor-based system 100 to support the create function is depicted in FIG. 3A. The patient views himself in the video window 121. As each exercise step is captured, the image is shown in one of the image window(s) 301 through 304. The control data 311 window enables voice recognition, sound output, skeleton display, echo cancellation, and other application features. The goal data 312 window can show the desired number of repetitions and the desired speed for the exercise. The status data 313 window can show instructions and help. Incorporating the voice recognition feature of the Kinect into the application, and optionally, the touch-screen features in some computer system embodiments, provides increased ease of use by both the patient and therapist.

A 3D image of the patient is taken for each exercise step using the Kinect camera. Along with the visual image of the patient, skeletal data is stored. One set of data contains the raw measurement of skeletal joint position and rotation collected by the Kinect NUI API, as disclosed for example in U.S. Pat. No. 7,961,910. A second set of data represents the therapeutic goals for the patient. The goals can include acceptable tolerances when comparing the stored 3D image to actual body position during exercise, the number of repetitions the patient should perform, and the cadence at which they should exercise. The therapist may specify additional parameters.

Figure 4:
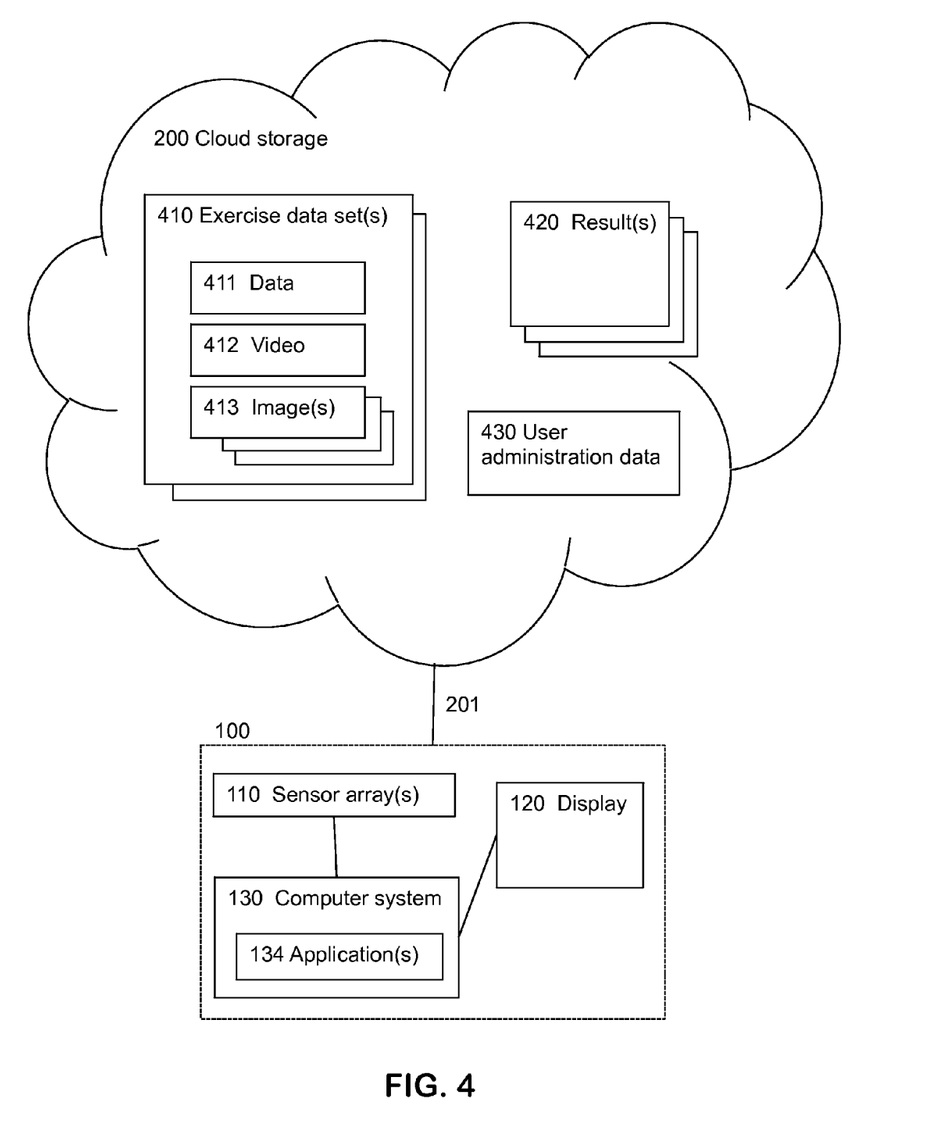
FIG. 4 illustrates schematically data in cloud storage, comprising exercise data sets, results, and user administration data.

The therapist optionally creates a video of the patient doing the exercise. The video serves as a cue to remind the patient what to do or what not to do. It is created using methods known in the art to convert a sequence of still images into a standard video file. Optionally, the therapist may specify additional audio or visual cues for the patient FIG. 4 depicts the exercise data set 410 that is generated each time the physical therapist creates a new exercise for a patient. This data set comprises a data file 411, a video file 412, and multiple image files 413. The exercise data set 410 may be stored locally on the sensor-based computer system 130 where the exercise is created. However, the exercise data set 410 can be transferred by the application 134 to cloud storage 200 to facilitate remote access using well-known data transfer mechanisms 201. In a preferred aspect of the present invention, an exercise that is created at the physical therapist's office can later be seamlessly used by the patient to exercise at home (or other remote location).

Review

The patient can review his list of assigned exercises, i.e., the exercises he created with his therapist. Each exercise contains steps, videos, and goals. Exercises are easily modified as treatment progresses, and the photos and videos of the patient provide an up-to-date visual reminder of how to do each step.

The user interface in FIG. 3A also supports review. The patient views her recorded video in the video window 121. She views each exercise step that was captured in the image window(s) 122. Desired goals are shown in the goal data 312, and reminders are shown in the status data 313 window.

As illustrated in FIG. 2B, the patient (or therapist) can also review the exercises from any secure Internet-enabled browser application 210 running on devices such as PC(s) 211, tablet(s) 212, or smartphone(s) 213. This enables more flexibility in which to review goals, images, and video.

Exercise

As the patient exercises, she can see herself move in real-time, she can see the desired next step, and she sees the moment she completes the step. Each step is tracked in three dimensions for accuracy. The patient's body position during exercise should algorithmically match the body position in the previously captured 3D image of each step within the desired tolerances. Each time a sequence of steps is completed, a repetition is tallied.

FIG. 4. schematically illustrates the exercise tracking application 134 retrieving exercise data set(s) 410 for a patient from cloud storage 200 using well known data transfer mechanisms 201.

The user interface in FIG. 3A would also support exercise on a sensor-based system 100, as depicted in FIG. 2A. The patient views himself in the video window 121. As each exercise step is completed, the image is highlighted in the corresponding image window. The example shown in FIG. 3A is of the patient in the video window 121 matching the step 1 image 301, which is highlighted as box 305. The goal data 312 window shows the number of repetitions accomplished and other relevant data such as the current exercise speed. The status data 313 window includes instructions, help, and encouragement. Encouragement to reach goals can use well-known gaming techniques such as real-time "carrots" to win points that are also displayed. Additional embodiments can include audio feedback instead of, or in addition to, a visual display.

Referring to FIG. 4, the results 420 of each exercise that the patient performs can be transferred by the application 134 to cloud storage 200 using well-known data transfer mechanisms 201. This embodiment allows the results of an exercise performed at home to be immediately viewed by the physical therapist in his office.

Results

Results are provided to the patient in real-time and are stored for later data aggregation and analysis. Patient-level clinical metrics include the time and date of exercise, data such as how many repetitions were completed, and where trouble spots occurred.

Figure 3B:
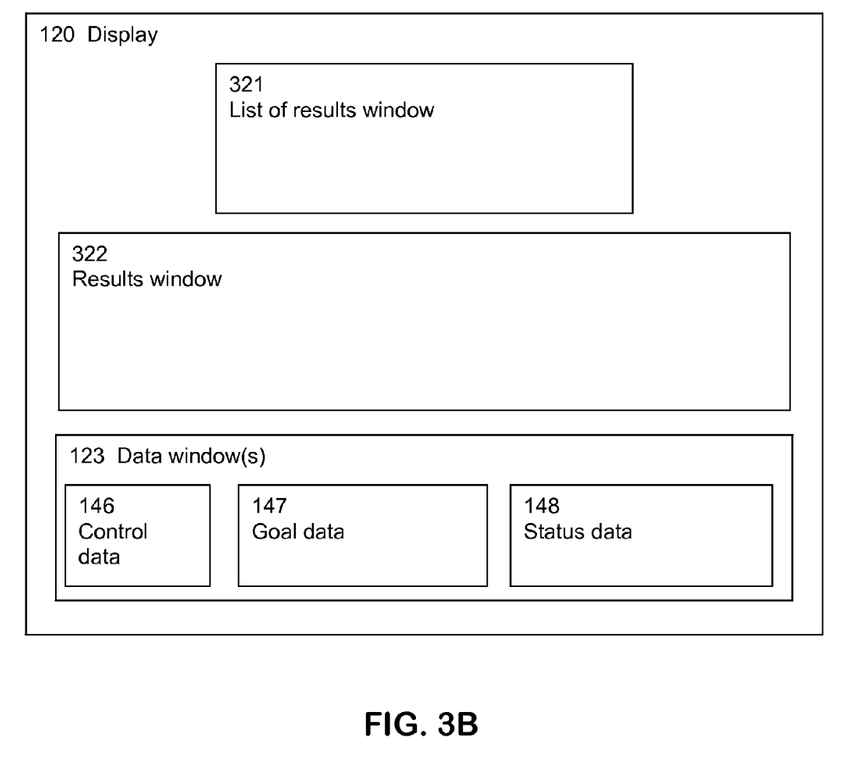
FIG. 3B illustrates schematically an example of a user interface to view the results of an exercise.

One embodiment of a user interface that would support results is depicted in FIG. 3B. A list of results representing each time a particular exercise was performed can be displayed in the results window 321. In one embodiment, a simple list of the resulting data for a specific exercise is displayed in the results window 322. Additional embodiments (not illustrated) can include graphical representations of progress across multiple exercises.

As illustrated in FIG. 2B, the patient (or therapist) can also review the results from any secure Internet-enabled browser application 210 running on devices such as PC(s) 211, tablet(s) 212, or smartphone(s) 213. This allows more flexibility in which to review results.

Data Collection

Data Storage

As illustrated in FIG. 4, application 134 data located in cloud storage 200 comprises one or more exercise data set(s) 410, one or more result(s) 420, and user administration data 430 for patients and physical therapists. Each exercise data set 410 comprises data 411, which could be stored in a file format such as XML; video 412, which could be stored in a file format such as AVI; and two or more images 413, which could be stored in a file format such as JPG. Result(s) 420 could be stored in a file format such as XML. Alternative formats may also be used, and are not limited to individual files; e.g. this data could be stored in a database. Image compression or other formats of varying complexity may optionally be used.

User administration data 430 is handled using industry standard techniques, enabled by cloud storage providers. All data is handled as private patient data. Procedures use standard techniques, such as encryption, to meet HIPAA requirements.

Application Inputs and Outputs

Figure 5:
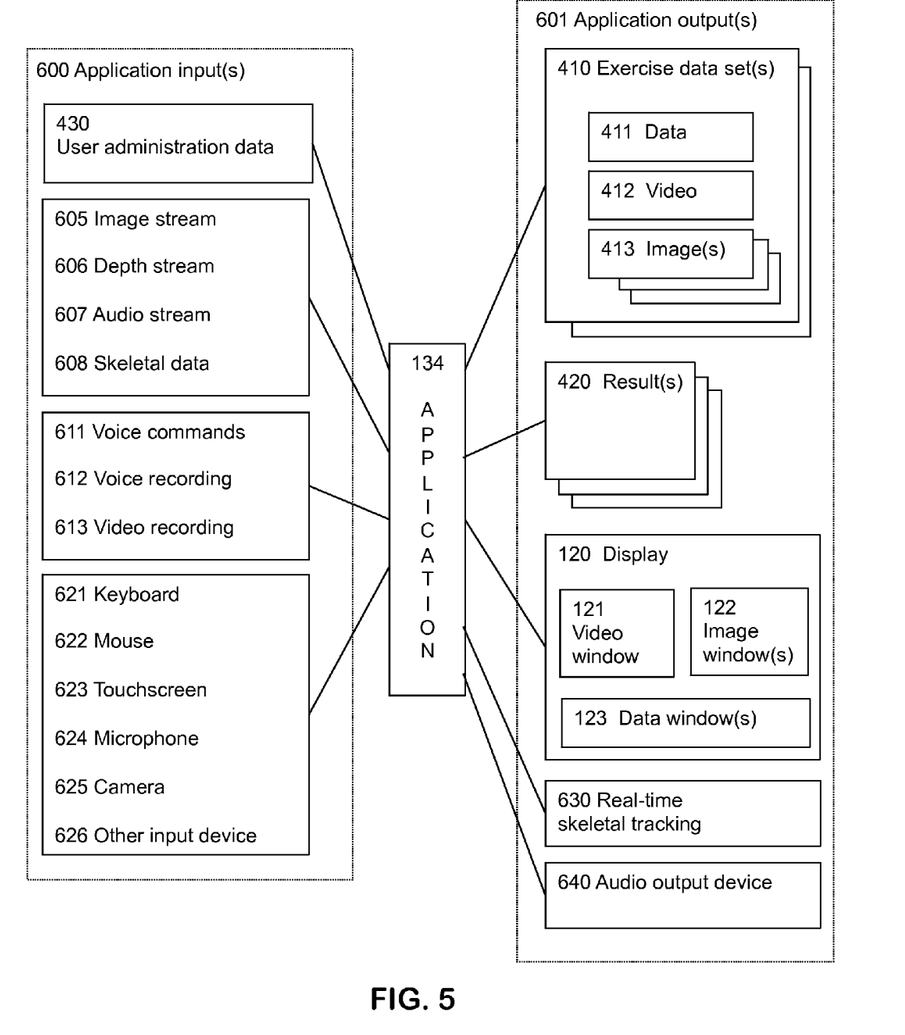
FIG. 5 illustrates schematically the inputs and output for the sensor-based system.

FIG. 5 depicts application inputs 600 and outputs 601. The data in an application is kept secure with input from the user administration 430. The NUI API (not shown) provides a coordinated image stream 605, depth stream 606, and audio stream 607 as input to the application 134. It also enhances the 3D depth stream to provide useful synchronized skeletal data 608.

Voice commands 611, voice recording 612, and video recording 613 can all be implemented in the application 134 using data from the NUI API's image stream 605 and audio stream 607. Application(s) 134 could also implement these three features in a variety of ways with alternative input devices, such as a standard microphone 624 and camera 625.

Other application input 600 can be from standard devices such as a keyboard 621, mouse 622, touchscreen 623, or any other input device 626 supported by the computer system, including gesture input received by the NUI API. This input is used to command the application and to set the goals and other data for each exercise.

Application outputs 601 comprise the exercise data set(s) 410 and the result(s) 420. In addition, an application can allow the patient to see recorded video, images, data, and results on the display 120. He can see himself during real-time skeletal tracking 630 (also shown in the video window 121 of the display 120). An audio output device 640 can play prerecorded audio cues.

Data Generation During Exercise Creation

In order to create a unique exercise for an individual, this invention captures the 3D data for each step of an exercise. As the physical therapist positions the patient to capture each step, the sensor (e.g., the Kinect) tracks the patient. When the therapist issues the step command, the current frame from the sensor provides the image and skeletal data for the exercise step. This step represents a new use of the skeletal data, which was originally developed to animate avatars.

In an improvement over the traditional method of using marked-up sketches of exercise steps, the physical therapist puts the patient into positions that cover the appropriate range of motion for that patient at that time. This allows de facto calibration of the exercise on the fly. However, even if the entire range of motion is not set in the exercise steps, the algorithm in FIG. 6 reduces injuries by encouraging the patient to stay within defined tolerances of the captured movement during exercise. The algorithm also checks to see if she is always moving towards the next step 707 during exercise.

In addition to data collected for each exercise step, data can be collected from the therapist for the exercise as a whole to set clear goals for the patient. In a basic embodiment, the goals represent the number of repetitions desired and the tolerances allowed for "almost" getting a step right. Other embodiments can contain data for the desired number of sets, the frequency of exercise (1/day, 3/week, etc), the pace for each repetition, the pace for the set, and other data used to encourage the user to exercise as prescribed.

Data During Exercise

As the patient exercises, the camera sensor tracks him. In FIG. 5, the application 134 gets a frame from the image stream 605 and displays it with real-time skeletal tracking 630 so that the patient watches himself exercise in the video window 121. The NUI API converts each frame from the depth stream 606 to skeletal data 608. The skeletal data is then compared to data in the next captured exercise step. If the joint position and rotation are within the specified tolerances that were set during capture, the step is matched. As shown in FIG. 3A, the matching step image 301 can be highlighted 305 in the user interface, giving a visual thumbs-up to the patient in real time.

The fact that the step is matched is noted in the results. In one embodiment, the individual real-time exercise frames may simply be discarded. Alternatively, in a telemedicine embodiment, the exercise frame can be relayed to the physical therapist for real-time viewing. In a third embodiment, each exercise frame is stored and then saved as a video for possible review by the physical therapist at a later time. Although the therapist would typically view only a summary of the exercise results, an unexpected advantage of this embodiment is that he could analyze a problem that occurs well into a long exercise session while skipping earlier parts of the session.

Figure 6:
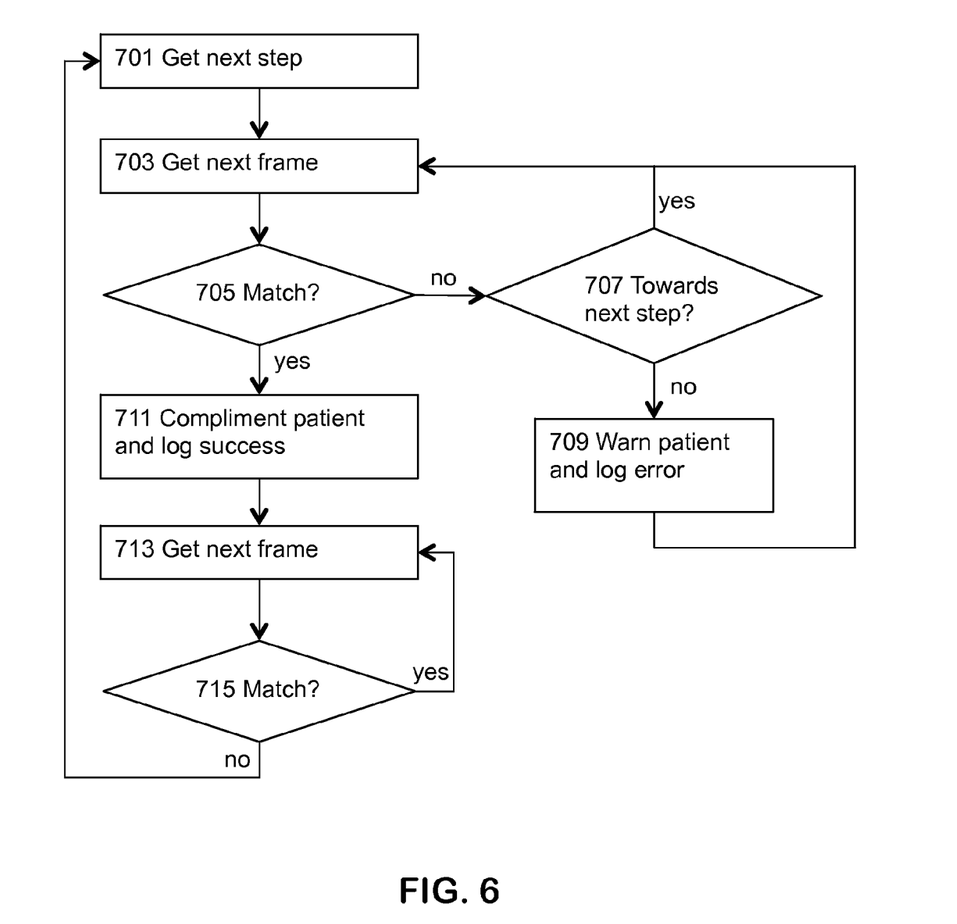
FIG. 6 illustrates schematically an algorithm to match frames of data to the desired exercise steps.

To match steps in the exercise, the application goes through an algorithm such as the one shown in FIG. 6. The application gets the first step 701 and next frame 703, and then it sees if they match 705 within tolerances.

If the match 705 succeeds, the application compliments the patient (for example, the image of the step is highlighted) and logs success 711. It gets the next frame 713 and checks for a match 715. For as long as match 715 succeeds, the application continues to get frames 713, assuming the patient is within the tolerance for the position in that step.

Timing can also be considered here because the patient should normally not stay in one position too long. However, at a typical video capture rate of 30 frames/second, several frames would be expected to match each position within tolerances. Once the patient no longer matches 715 the step, the algorithm goes to get the next step 701 and the next frame 703.

If the match 705 fails, the application checks to see if the patient is moving towards the next step 707. This prevents the patient from going beyond the range of movement the therapist specified (for example, lifting their arm too high). If the patient is not going towards the next step 707, the patient is warned (for example, via a written message in a data window or a message played on an audio output device), and an error 709 is logged. The application gets the next frame 703.

This process continues in real-time—when all the steps for one exercise are completed, a repetition is tallied (for example, the current tally is shown in a data window); when all the repetitions are completed the user is again complimented (for example, a voice message on an audio output device says "congratulations"). Real-time targeted feedback is provided to the patient in a variety of ways, although it is preferred not to flood them with unnecessary or irrelevant information about their body position.

Data Aggregation and Analysis

An unexpected advantage comes from aggregating data in cloud storage 200. Patient result data can easily be aggregated and analyzed for an individual patient, for a medical practice, or to develop metrics for best practices in rehabilitation protocols.

Figure 7:
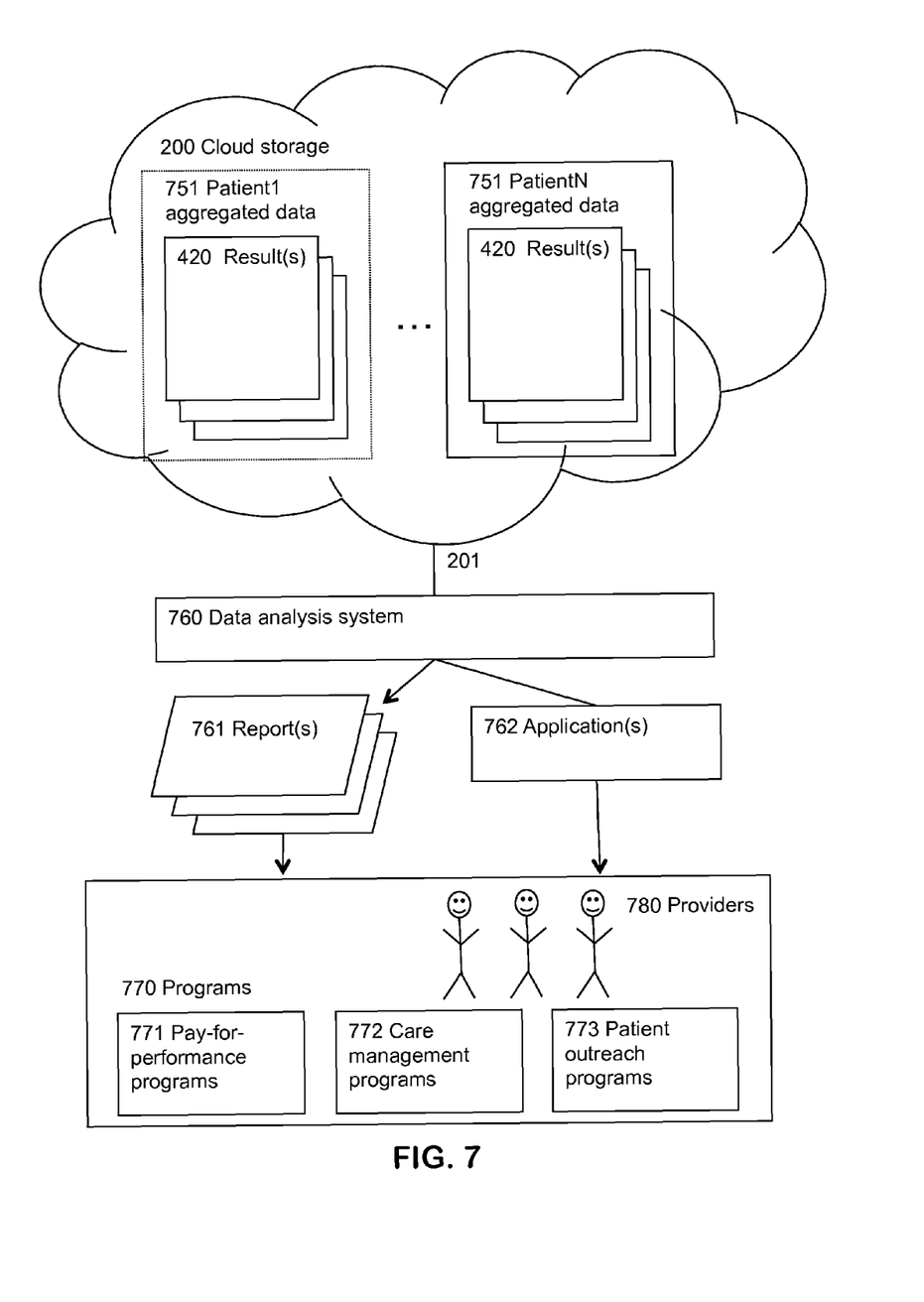
FIG. 7 illustrates schematically data aggregation and analysis embodiments and use cases.

As illustrated in FIG. 7, results 420 can be aggregated for each patient 751 as they progress in therapy. A data analysis system 760 can aggregate results across multiple patients with similar goals, generating reports 761 or providing application 762 interfaces to the analysis.

Compliance and performance reports 761 can be generated with clinical data for quality measurements. Providers 780 can leverage key progress data to track the effectiveness of evidence-based treatment plans. They can also use this data to predict high-risk patients and to optimize chronic care management. Provider organizations can compare quality and performance measurements between providers to optimize treatment and patient care. Programs 770, such as the Physician Quality Incentive Programs or other pay-for-performance 771 initiatives, use data to monitor and track quality improvements. The efficacy of patient outreach 773 and care management 772 programs can be improved with patient data, thus institutionalizing best practices in these fields.

Applications 762 can encourage patients through established techniques such as leader boards, or provide an interface to social networking groups. An application 762 could track compliance with treatment plans and generate clinical alerts when problems arise.

Among the many advantages of a data analysis system 760 is that quality improvements to physical therapy treatment plans result in better patient compliance, better patient health, and lower individual healthcare costs. The healthcare team can be more proactive in the way they manage chronic conditions by optimizing rehabilitation protocols. Overall health care costs are reduced by helping to minimize the effect of chronic conditions and by helping physicians and the care team stay within reimbursement conditions set by payers.

Accuracy

Without three-dimensional data comparison, a sensor-based system cannot accurately ascertain whether the patient is performing the exercises to the exact specification that the therapist requires for rehabilitation. Using a depth sensor with the camera as described herein enhances accuracy in many situations, such as when an arm should be in front of the body instead of on the side. Joint tracking can notify the patient when any joint is out of position, such as when the patient is shrugging his shoulders during an exercise. Depending on the exercise, the physical therapist may create exercises where the sensor is on the side of the patient or behind the patient.

There are cases where the joints and bones of the skeleton are not seen from certain angles. An example is when the camera is in front of the patient to track arm movements, but the patient incorrectly arches his back. One embodiment in these circumstances is to have the physical therapist provide a written reminder on the display. A second embodiment would be to have the therapist record an audio cue to remind the patient. This real-time feedback assists the patient in better matching the desired outcome.

Additional embodiments to increase accuracy under some circumstances, such as when part of the body is occluded, include using multiple Kinect sensors, using props, using markers, or using two or more cameras to produce high-resolution three-dimensional measurements. If props or markers are used, they may or may not be attached to the body. As noted in the USC study, a low-cost Kinect is easier to use and is more economical for a home or clinical setting than a high-cost, marker-based multi-camera system. These tradeoffs in costs should be considered in such additional embodiments.

Advantages and Unexpected Results

This invention delivers a number of advantages and unexpected results. Some of these advantages and unexpected results follow from the capture of each exercise step for each individual patient. Proceeding in such a direction departs both from the instructional legacy of physical therapy and group exercise, and also from the gaming heritage of prior fitness programs:

Instructional Legacy of Physical Therapy

Physical therapy home instruction has progressed from stick figures, to paper sketches, to photographs of an ideal or generic model performing an exercise, to videos of an ideal or generic model performing an exercise. Some contemporary prototypes using the Kinect to replicate this earlier model by tracking a patient who attempts to follow a pre-determined, "ideal" or "generic" model for a particular exercise. The patient is corrected when she deviates from the "ideal" or "generic" standard.

By contrast, in the present invention each exercise is created uniquely for each patient, and the patient is compared to his own personalized standard, rather than to some "ideal" or "generic" standard. This is of substantial benefit in treating individual injuries. Of perhaps even greater benefit is that, using the novel approach, multiple injuries or limitations can be readily taken into account as each exercise is created by the physical therapist and patient. Multiple injuries are frequently mentioned as being one of the most difficult situations to address in physical therapy. Unfortunately, multiple injuries are also fairly common. But multiple injuries cannot be efficiently addressed using a one-size-fits-all "ideal" or "generic" standard.

Another distinct advantage of the novel approach is that the exercises are readily modified and re-created as the patient improves. Thus all patients can progress at their own individual pace until they reach the desired goal. Again, this approach is not easily accommodated by prior techniques that use an ideal or generic model.

Gaining Heritage of Prior Fitness Programs

The Kinect has allowed many developers skilled in the art of software to create many new inventions. The Kinect was originally designed as an accessory for Xbox gaming applications. The Wii and the PS3 also have gaming accessories. As developers have used these accessories in new fields, such as rehabilitation or physical therapy, the developments have typically taken on a "gaming" flavor as a result of this heritage, even when they are considered to be "serious games" because of their target market. These applications usually attempt to make rehabilitation more fun and interesting, and many of them undoubtedly achieve that goal.

The present invention, however, does not attempt to create a game, which can be defined as an application that presents avatars in a virtual environment. Although the invention is engaging and presents the patient with goals, there is no need for a virtual game environment. Instead, the patient sees himself in a virtual mirror (i.e., a video representation that reverses left and right), attempting to match each step he himself had earlier been positioned in. This approach results in fewer injuries because the patient is only trying to perform the assigned steps, and preferably is not distracted by the goals found in a game. In addition, since the exercises are captured specifically for each patient, no game elements need be present, game elements that could encourage some movement that is inappropriate to the particular patient. Older people will find the invention easy to use because they only see themselves, not a game element or an avatar. This helps them better remember what they are supposed to do. Alternative embodiments employ other means to engage and maintain the patient's interest and motivation, including for example overlaying a cartoon character on the patient's face, other types of augmented reality displays known in the art, providing a thematic background for exercise, and other engaging special effects.

The complete disclosures of all references cited in this specification are hereby incorporated by reference. Also incorporated by reference is the complete disclosure of Applicants' co-pending U.S. provisional patent application Ser. No. 61/727,800, filed Nov. 19, 2012. In the event of an otherwise irreconcilable conflict, however, the present specification shall control.

What is claimed:

1. A method for a person and a trainer to create an exercise that is uniquely tailored for the person; and for the person to perform the exercise at a later time; and to provide the person with immediate feedback concerning the performance of the exercise; said method comprising the steps of:
   (a) creating the exercise by:
      (i) the trainer choosing an exercise that is uniquely tailored for the person, wherein the exercise comprises a set of several target positions for the person's body;
      (ii) for one of the target positions of the set, placing the person's body into the target position under the supervision of the trainer;
      (iii) using a camera with a depth sensor to capture a three-dimensional digital representation of the person's body or a portion of the person's body while the person's body is placed at the target position; wherein substep (iii) occurs simultaneously with substep (ii); and
      (iv) repeating substeps (ii) and (iii) for each target position in the set of target positions; whereby a three-dimensional digital representation is captured for all target positions comprising the uniquely tailored exercise;
   (b) converting the three-dimensional digital representation of the target positions into target data that numerically represent the position of pertinent aspects of the person's bones and joints at each of the set of target positions, and recording the target data;
   (c) performing the exercise, at a time later than step (b), wherein the person moves the person's body through a set of actual positions in which the person attempts to duplicate each of the target positions;
   (d) capturing a three-dimensional digital representation of the person's body or a portion of the person's body as the person moves through the set of actual positions while performing the exercise; wherein steps (c) and (d) occur simultaneously;
   (e) converting the three-dimensional digital representation of the actual positions into actual data that numerically represent the position of pertinent aspects of the person's bones and joints at each of the set of actual positions;
   (f) determining whether the actual data match the target data within pre-determined tolerances; and
   (g) providing the person with automated, real-time feedback whether the actual data match the target data within the pre-determined tolerances: wherein the person is provided encouragement if the exercise is being performed properly within the pre-determined tolerances; or wherein the person is provided suitable information to permit the person to make immediate adjustments to the person's exercise performance to better match the target positions if the exercise is not being performed properly within the pre-determined tolerances; or both.

2. The method of claim 1, additionally comprising a step wherein the trainer sets one or more goals for the person in performing the exercise, and wherein the feedback provided to the person includes information regarding the person's progress towards the one or more goals.

3. The method of claim 2, additionally comprising the step of performing an automated analysis comparing the actual data to the goals, and wherein the results of the automated analysis are stored as result data.

4. The method of claim 3, wherein the result data comprise one or more of the following: timestamps; elapsed time; accuracy; number of repetitions; and video or still images of one or more instances of the person's performing the exercise improperly, outside the pre-determined tolerances.

5. The method of claim 1, wherein the real-time feedback comprises providing to the person one or more visual or audio cues.

6. The method of claim 1, wherein the real-time feedback comprises displaying to the person one or more visual cues in an augmented reality display.

7. The method of claim 1, wherein said feedback-providing step comprises displaying to the person a video showing a virtual mirror image of the person moving through each of the target positions.

8. The method of claim 1, wherein said feedback-providing step comprises displaying to the person images of the person properly positioned in each of the target positions, and indicating whether the person's actual position properly matches the target positions, within the pre-determined tolerances.

9. The method of claim 1, wherein said feedback-providing step comprises real-time audio and visual communication between the trainer and the person, wherein the trainer and the person are located at physically separate locations when the person performs the exercise.

10. The method of claim 2, wherein said feedback-providing step comprises providing the person with visual or audio progress measurements that compare the actual data to the goals.

11. The method of claim 3, additionally comprising the step of transmitting the result data to remote storage, and storing the result data on remote storage.

12. The method of claim 11, additionally comprising the step of retrieving and displaying the remotely-stored result data in a format that is convenient to be reviewed and analyzed by a human.

13. The method of claim 12, additionally comprising a step wherein the trainer reviews and analyzes the result data; and wherein, following the analysis, the trainer modifies the goals, or the trainer modifies the feedback, or the trainer modifies the exercise, or the trainer creates one or more new exercises for the person.

14. The method of claim 12, additionally comprising a step wherein the trainer reviews and analyzes the result data, wherein the trainer is a medical professional, and wherein the trainer uses the result data to track the person's compliance with a prescribed treatment plan.

15. The method of claim 12, additionally comprising a step wherein result data for a plurality of persons are aggregated and analyzed either automatically or by one or more medical professionals, and wherein the results of the analysis are thereafter used to optimize treatment protocols, care management, or both.

16. The method of claim 12, additionally comprising the step of integrating the result data with one or more social networking tools to provide support to the person.

17. The method of claim 1, wherein the person has multiple injuries or multiple physical problems, and wherein the exercise is created by the trainer to account for the multiple injuries or multiple physical problems.

18. The method of claim 1, wherein steps (c) and (g) are performed at a location that is physically remote from the location where step (a) is performed.

19. The method of claim 1, wherein the trainer is a physical therapist, and wherein the person is a physical therapy patient.

20. The method of claim 1, wherein the trainer is an athletic coach or personal trainer, and wherein the person is an athlete.

* * * * *